(12) United States Patent
Auerbach et al.

(10) Patent No.: US 8,492,108 B2
(45) Date of Patent: Jul. 23, 2013

(54) METHODS OF TREATING ANEMIA AND RED BLOOD CELL DYSFUNCTION WITH LECITHIN CHOLESTEROL ACYLTRANSFERASE

(76) Inventors: Bruce J. Auerbach, Ann Arbor, MI (US); Reynold Homan, Ann Arbor, MI (US); Brian Krause, Ann Arbor, MI (US)

( * ) Notice: Subject to any disclaimer, the term of this patent is extended or adjusted under 35 U.S.C. 154(b) by 0 days.

(21) Appl. No.: 13/377,586

(22) PCT Filed: Jun. 14, 2010

(86) PCT No.: PCT/US2010/038494
§ 371 (c)(1),
(2), (4) Date: Jan. 12, 2012

(87) PCT Pub. No.: WO2010/144904
PCT Pub. Date: Dec. 16, 2010

(65) Prior Publication Data
US 2012/0107298 A1    May 3, 2012

Related U.S. Application Data (60) Provisional application No. 61/186,668, filed on Jun. 12, 2009, provisional application No. 61/241,223, filed on Sep. 10, 2009.

(51) Int. Cl.
*C12Q 1/48*    (2006.01)
(52) U.S. Cl.
USPC .......................................................... 435/15
(58) Field of Classification Search
USPC ............................................ 435/15; 514/7.4
See application file for complete search history.

(56) References Cited

U.S. PATENT DOCUMENTS

| | | | |
|---|---|---|---|
| 6,635,614 B1 * | 10/2003 | Santamarina-Fojo et al. | 514/7.4 |
| 2008/0096900 A1 * | 4/2008 | Kayser et al. | 514/255.05 |
| 2009/0081182 A1 * | 3/2009 | Boone et al. | 424/94.5 |

FOREIGN PATENT DOCUMENTS

| | | | |
|---|---|---|---|
| WO | 97/17434 | A2 | 5/1997 |
| WO | 01/05943 | A2 | 1/2001 |
| WO | 2009/015314 | A2 | 1/2009 |

OTHER PUBLICATIONS

Suda T. et al. Alterations in Erythrocyte Membrane Lipid and its Fragility in a Patient with Familial LCAT Deficiency. The J of Medical Investigation 49(3-4)147-155, Aug. 2002.*
Mehlum A. et al. Mice Overexpressing Human LCAT . . . APMIS 105(11)861-868, 1997.*
Cooper, Richard A. et al., "An Analysis of Lipoproteins, Bile Acids, and Red Cell Membranes Associated with Target Cells and Spur Cells in Patients with Liver Disease", J. Clin. Invest. (The Journal of Clinical Investigation),1972, pp. 3182-3192, vol. 51, No. 12.
Muryama, Naoki et al., "Decreased sodium influx and abnormal red cell membrane lipids in a patient with familial plasma lecithin:Cholesterol acyltransferase deficiency," Am. J. Hematol. (American Journal of Hematology), 984, pp. 129-137, vol. 16, 1984.
Powell, Lawrie W. et al., "The Relationship of Red Cell Membrane Lipid Content to Red Cell Morphology and Survival in Patients with Liver Disease", Aust. N. Z. J. Med. (Australian and New Zealand Journal of Medicine), vol. 5, No. 2, 1975, pp. 101-107.
Rousset, Xavier et al., "Lecithin:Cholesterol Acyltransferase: From Biochemistry to Role in Cardiovascular Disease," Curr. Opin. Endocrinol. Diabetes Obes. ( Current Opinion in Endocrinology, Diabetes, and Obesity), 2009, pp. 163-171, vol. 16, No. 2.
Clew R.H. et al., "Correlation of the Fatty Acid Composition and Fluid Property of the Cholesteryl Esters in the Serum of Nigerian Children with Sickle Cell Disease and Healthy Controls", Prostaglandins Leukotrienes and Essential Fatty Acids, 2003, pp. 61-68, vol. 68.
Lane S B et al., "Characterization of Lecithin:Cholesterol Acyltransferase Expressed in a Human Ling Cell Line", Protein Expression and Purification, 2004, pp. 157-164, vol. 36, No. 2.
Suda T. et al., "Alterations in Erythrocyte Membrane Lipid and its Fragility in a Patient with Familial Lecithin:Cholesterol Acyltransferase (LCAT) Deficiency". J. Med. Invest, 2002, pp. 147-155, vol. 49.
PCT/US2010/038494 International Search Report, Sep. 29, 2010.

* cited by examiner

*Primary Examiner* — Ralph Gitomer

(57) ABSTRACT

Disclosed are methods for treating conditions characterized by anemia or red blood cells dysfunction by administering an agent that increases the level of endogenous LCAT or LCAT activity. Additionally disclosed are methods of treating conditions wherein red blood cells have reduced function in relation to deformability, oxygenation, increased adhesion and aggregability, reduced nitric oxide function, or decreased life-span, increased free cholesterol, or abnormal phospholipid content. Also disclosed are methods for treating conditions characterized by an abnormal concentration of free cholesterol in red blood cells and methods of normalizing the free cholesterol content of red blood cells.

10 Claims, 3 Drawing Sheets

METHODS OF TREATING ANEMIA AND RED BLOOD CELL DYSFUNCTION WITH LECITHIN CHOLESTEROL ACYLTRANSFERASE

CROSS-REFERENCE TO RELATED APPLICATIONS

This application is a National Phase application of PCT/US2010/038494 filed Jun. 14, 2010, and claims priority to U.S. Provisional Application Ser. No. 61/186,668 filed Jun. 12, 2009, and U.S. Provisional Application Ser. No. 61/241,223 filed Sep. 10, 2009. The entire content of U.S. Provisional Application Ser. No. 61/186,668 and U.S. Provisional Application Ser. No. 61/241,223 is incorporated herein by reference.

FIELD OF INVENTION

This invention relates generally to the field of medicine, and in particular, the treatment of diseases characterized by anemia and/or red blood cells that have abnormal function in terms of deformability, oxygenation, aggregation, nitric oxide metabolism, or life-span.

BACKGROUND

The quality and quantity of red blood cells (RBC) in the blood stream is often degraded during periods of increased physical stress, resulting in anemia and enhanced risks of morbidity and mortality. Physical stresses that have been linked to the development of anemia include autoimmune diseases, major surgery, trauma, infectious diseases, cancer, critical illness, diabetes, liver diseases, kidney disease, heart failure, and parasitic diseases. Systemic inflammation is a characteristic common to all these situations as evidenced by the presence of increased levels of inflammatory cytokines in the circulation. Even in persons predisposed to anemia because of a hemoglobinopathy, for example sickle cell disease or thalassemia, inflammatory cytokine levels are frequently elevated and can exacerbate the disease symptoms, particularly during crisis episodes.

One consequence of elevated inflammatory cytokine levels is a reduction in the hepatic production of the enzyme lecithin:cholesterol acyltransferase (LCAT). Normally, LCAT is released into the plasma from the liver to facilitate plasma lipid turnover and maintain the balance of cholesterol and phospholipids in the blood and the tissues perfused by blood. Excess cholesterol is removed from tissues, such as arteries, and delivered to the liver for excretion in bile by a process known as reverse cholesterol transport (RCT). In the first step of RCT, cholesterol passes from tissue cells to high-density lipoproteins (HDL) in the circulation. In the second step, the enzyme LCAT enhances the cholesterol-carrying capacity of HDL by catalyzing the transesterification of a fatty acid from phosphatidylcholine (PC) (also known as lecithin), to cholesterol to form cholesteryl ester (CE). The CE product accumulates in the HDL interior until it is removed at HDL-receptors in the liver. The CE delivered to the liver by HDL is converted to cholesterol and bile acids that are excreted in the bile.

The health consequences of diminished plasma LCAT activity are most evident in persons with Familial LCAT Deficiency (FLD), a rare genetic disease in which plasma LCAT activity is absent. The absence of LCAT activity results in greatly diminished levels of plasma CE, reflected in decreased HDL and low-density lipoprotein, and in the accumulation of excess LCAT substrate in plasma. The major health consequences of FLD are reduced vision resulting from a diffuse build-up of lipid in the corneas, eventual kidney failure due to renal lipid accumulation (glomerulosclerosis), and hemolytic anemia.

Distortions in the plasma lipoprotein lipid compositions due to lipid metabolic disorders such as those resulting from low LCAT activity have been associated with changes in the lipid content of RBC. A shift in RBC lipids in response to plasma lipid changes can alter RBC performance and survival since these properties are dependent on cellular lipid content. The types of RBC lipid changes that can occur are evident in FLD subjects where the RBC are enriched in cholesterol and PC and diminished in sphingomyelin (SM) content. Evidence that these RBC lipid abnormalities depend on disturbances in plasma lipoprotein lipids as a result of LCAT deficiency was obtained in an experiment were a temporary normalization of RBC cholesterol content occurred following infusion of normal plasma into an FLD subject (Muryama et al. Am. J. Hematol. 16:129-137, 1984). This temporary normalization of the RBC lipids could be due to the replenishment of LCAT, HDL, apolipoprotein A-I or other plasma factors that are absent or greatly reduced in patients with FLD.

No link between anemia and LCAT activity is seen in less severe cases of diminished plasma LCAT activity. For example, patients with fish eye disease, a milder form of LCAT deficiency, exhibit less than 30% of normal plasma LCAT activity but have normal hemoglobin and hematocrit (Rousset et al. Curr. Opin. Endocrinol. Diabetes Obes. 16:163-171, 2009). Similarly, studies in subjects with liver disease found no correlation between lowered LCAT activity and anemia (L W Powell et al. (1975) Aust. N. Z. J. Med. 5:101-107), or between LCAT activity and RAC lipid abnormalities. (R A Cooper et al. (1972) J. Clin. Invest. 51:3182-3192).

Figure 1:
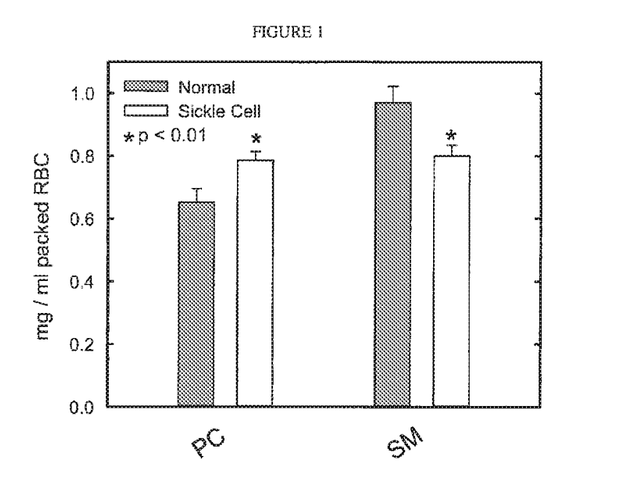
FIG. 1 shows phospholipid composition of RBC from normal subjects and from subjects with Sickle Cell Disease.

Although there is evidence of deleterious lipid alterations in RBC in persons under physical stress that are similar to those detected in FLD patients, there is no apparent relationship between LCAT and RAC level or lipids. Examples of anomalous RBC lipid composition include reports of increased PC/SM ratio in RBC from persons with liver disease and in persons with dyslipidemia due to lipoprotein lipase deficiency or Tangier Disease. We (FIG. 1) and others have also found an increase in the PC/SM ratio in RAC from sickle disease patients who are not in crisis. Furthermore, there are reports of cholesterol enrichment in RBC from persons with diabetes, heart disease (including acute coronary syndromes), hypercholesterolemia, sickle cell anemia, and in persons after space flight.

The consequences of modified RAC lipid composition are not fully known but in the case of elevated RBC cholesterol there is evidence that activities of membrane proteins become abnormal. Cholesterol-enriched RBC from liver disease patients exhibit reduced activities of Mg++-ATPase and acetylcholine esterase. Cholesterol enrichment has been linked to enhanced transfer of phosphatidylserine from the inner to the extracellular membrane surface, which is a signal for enhanced clearance of RAC by the reticulo-endothelial system. Increased RBC cholesterol can reduce RBC deformability and induce abnormal RBC morphologies, both of which can impair RBC transit through the capillaries. Transmembrane gas exchange, an essential RBC function, is also impacted by cholesterol elevation.

The current evidence suggests abnormal RAC lipid compositions can have a deleterious effect on red blood cell function and therefore there is a need for methods to normalize RAC lipid composition and methods to treat red blood cell dysfunction.

SUMMARY OF THE INVENTION

There is no consensus in the literature as to the correlation between HDL-C and endogenous LCAT activity. We made the surprising discovery that an increase in plasma LCAT levels by injection of recombinant human LCAT rapidly results in a removal of cholesterol from tissues. Additionally, HDL-C was rapidly increased. Given the equilibrium that exists between HDL and RBCs, these surprising results indicate that the infusion of LCAT could also be used to rapidly correct blood cell lipid abnormalities and improve blood cell function.

Plasma HDL-C levels are often reported to be reduced in cases of physical stress, for example: autoimmune diseases, major surgery, trauma, infectious diseases, cancer, critical illness, diabetes, liver diseases, kidney disease, heart failure and parasitic diseases, and may be an important factor in the distortion of RBC lipid content, in light of the direct lipid interchange between RBC and lipoproteins. Anemia is highly prevalent in the cases where HDL is reduced.

The present disclosure relates to methods modulating the lipid content of red blood cell membranes by increasing LCAT concentration and/or activity above normal human LCAT concentration and/or activity by administering a therapeutically effective dose of LCAT.

One embodiment of the disclosure is a method of treating a patient having a condition characterized by red blood cell dysfunction comprising administering to the subject a therapeutically effective amount of LCAT.

Another embodiment is a method of treating a patient having a condition characterized by anemia or red blood cells with reduced deformability, reduced oxygenation, reduced nitric oxide function, increased adhesion and/or aggregation, or decreased life-span, or any combination thereof comprising administering to the patient in need thereof, a therapeutically effective amount of LCAT.

In another embodiment, the method of treating a patient having a condition characterized by anemia or red blood cells with reduced deformability, reduced oxygenation, reduced nitric oxide function, increased adhesion and/or aggregation, or decreased life-span, or any combination thereof comprises determining a baseline RBC deformability or RBC oxygenation or RBC aggregation or adhesion or RBC life-span; administering to the patient in need thereof, a therapeutically effective amount of LCAT; and determining the changes following LCAT administration wherein an increase in RBC deformability or RBC oxygenation or decreased RBC aggregation or adhesion or increased RBC life-span indicates an improvement in the condition.

In some embodiments, the condition treated is sickle cell disease, diabetes, thalassemia, rheumatoid disease, autoimmune disease, arthritis, liver disease, cirrhosis, hepatitis, acanthosytosis, sepsis, dementia, anemia, or microvascular disorders, inflammatory disorders, parasitic disease, erectile dysfunction, cancer, pre-eclampsia, critical illness or trauma.

Another embodiment is a method of treating a patient having a condition characterized by a high level of FC in RBC membranes comprising administering to subject, in need thereof, a therapeutically effective amount of LCAT. Another embodiment is a method of treating a patient having a condition characterized by a high level of FC in RBC membranes comprising determining a baseline ratio of FC to PL; administering to subject, in need thereof, a therapeutically effective amount of LCAT; and determining the ratio of FC to PL following administration of LCAT wherein a decrease in the ratio of FC to PL indicates an improvement in the condition. Another embodiment is a method of reducing the FC content of a blood cell in a patient comprising administering to the patient a therapeutically effective amount of LCAT.

Another embodiment is a method of treating a patient having a condition characterized by an increased PC/SM ratio in RBC membranes comprising administering to subject, in need thereof, a therapeutically effective amount of LCAT. Another embodiment is a method of treating a patient having a condition characterized by an increased PC/SM ratio in RBC membranes comprising determining a baseline ratio of PC to SM; administering to subject, in need thereof, a therapeutically effective amount of LCAT; and determining the ratio of PC to SM following administration of LCAT wherein a decrease in the ratio of PC to SM indicates an improvement in the condition. Another embodiment is a method of reducing the PC/SM ratio of a blood cell in a patient comprising administering to the patient a therapeutically effective amount of LCAT.

DETAILED DESCRIPTION

The term "therapeutically effective amount", as used herein, means the amount of LCAT which will elicit the desired therapeutic effect or response when administered in accordance with the desired treatment regimen, A preferred therapeutically effective amount is an amount of LCAT that increases the level of plasma LCAT to above normal levels.

As used herein "LCAT level" refers to the plasma concentration of LCAT.

As used herein, a "normal level" of LCAT means the plasma concentration of LCAT that is present in average healthy untreated subject not currently on any medication which might alter LCAT levels. "Normal level" and "endogenous level" are used interchangeably herein.

For the avoidance of doubt, references herein to "treatment" or "treating" include curative, palliative and prophylactic treatment.

"Subject" and "Patient" are used interchangeably.

Between as used herein with reference to effective amount or unit dosage is inclusive, e.g., "between 1 mg and 5000 mg" includes 1 mg and 5000 mg.

"From" as used herein with reference to effective amount or unit dosage is inclusive, e.g., "from 1 mg to 5000 mg" includes 1 mg and 5000 mg.

"FC" is an abbreviation for free cholesterol and as used herein means non-esterified cholesterol.

"Nitric oxide function" means RBC mediated processes which are dependent on nitric oxide including nitric oxide production, nitric oxide delivery to the microvasculature, inhibition of platelet and leukocyte adhesion, vasodilation, RBC deformability and RBC survival.

"PC" is an abbreviation for phosphatidylcholine.

"SM" is an abbreviation for sphingomyelin

"RBC deformability" means the ability of cells to adapt their shape to the dynamically changing flow conditions in order to minimize their resistance to flow, and to enable their passage through small blood vessels. Reduced deformability equates with increased rigidity.

A "gene therapy vector" is an agent which is used to incorporate and actively express a gene of interest in chromosomes in parenchymal tissue cells. For example an adenovirus engineered to carry the human LCAT gene.

"Osmotic fragility" means a cell's sensitivity to rupture due to changes in surrounding osmotic pressure.

"RBC aggregability" means the ability to form multicellular aggregates, normally in a rouleaux shape, in the presence of plasma proteins or other macromolecules.

"LCAT" is used interchangeably with "lecithin-cholesterol acyltransferase"

"LCAT" or "LCAT polypeptide" when used herein encompass native sequence LCAT, LCAT variants, modified LCAT, and chimeric LCAT. In specifying amino acid positions in the LCAT sequence, reference is made to SEQ ID NO: 1

```
(Genbank Accession No. AAB34898)
                          Human LCAT SEQ ID NO: 1
FWLLNVLFPP  HTTPKAELSN  HTRPVILVPG  CLGNQLEAKL

DKPDVVNWMC  YRKTEDFFTI  WLDLNMFLCL  GVDCWIDNTR

VVYNRSSGLV  SNAPGVQIRV  PGFGKTYSVE  YLDSSKLAGY

LHTLVQNLVN  NGYVRDETVR  AAPYDWRLEP  GQQEEYYRKL

AGLVEEMHAA  YGKPVFLIGH  SLGCLHLLYF  LLRQPQAWKD

RFIDGFISLG  APWGGSIKPM  LVLASGDNQG  IPIMSSIKLK

EEQRITTTSP  WMFPSRMAWP  EDHVFISTPS  FNYTGRDFQR

FFADLHFEEG  WYMWLQSRDL  LAGLPAPGVE  VYCLYGVGLP

TPRTYIYDHG  FPYTDPVGVL  YEDGDDTVAT  RSTELCGLWQ

GRQPQPVHLL  PLHGIQHLNM  VFSNLTLEHI  NAILLGAYRQ

GPPASPTASP  EPPPPE
```

Specific amino acids in the native human LCAT protein sequence are described using single letter amino acid designation followed by the position in the protein sequence, for example W2 indicates that position 2 is a tryptophan. To represent a substitution at a particular position, the substituted amino acid follows the position, for example W2Y indicates that the tryptophan at position 2 is replaced with a tyrosine.

A "native sequence LCAT" comprises a polypeptide having the same amino acid sequence as a LCAT derived from nature. Thus, a native sequence LCAT specifically encompasses naturally occurring truncated forms of LCAT, and naturally-occurring allelic variants of LCAT, naturally-occurring variant forms (e.g., alternately spliced forms). The preferred native sequence LCAT is a mature native sequence LCAT.

"Modified LCAT" means a polypeptide wherein one or more amino acids in the native LCAT polypeptide is substituted with another amino acid, or one or mom amino acids is added to a portion of the native polypeptide, including, but not limed to, the N-terminal or C-terminal amino acid. For example and without limitation the modified LCAT may be a modified LCAT protein as described in U.S. patent application Ser. No. 12/179,815. In other embodiments the one or more amino acid is substituted with a conservative substitution. Non-limiting exemplary conservative substitutions are provided in Table 2. In other embodiments, the one or more amino acids is substituted with a non-naturally occurring amino acid. In addition, modified LCAT polypeptides include derivatives of LCAT or modified LCAT. These derivatives may, for example, improve the solubility, absorption, biological half life, of the polypeptides. Derivatives of polypeptides are well known in the art. One of skill in the art would know how to derivatize polypeptides to improve their pharmacologic properties.

TABLE 2

| Original Residue | Exemplary Conservative Substitutions |
|---|---|
| A | G, S |
| R | K |
| N | Q, H |
| D | E |
| C | S |
| Q | N |
| E | D |
| G | A, P |
| H | N, Q |
| I | L, V |
| L | I, V |
| K | R, Q, E |
| M | L, Y, I |
| F | M, L, Y |
| S | T |
| T | S |
| W | Y |
| Tyr | W, F |
| Val | I, L |

The present disclosure is directed to methods of treating patients having a condition characterized by anemia or red blood cell dysfunction comprising administering to a patient in need there of an agent which increases the activity of LCAT or increases the plasma level of LCAT or both. The LCAT level and/or LCAT activity can be increased by any means available. This includes, without limitation, direct administration of LCAT, expression of LCAT through gene therapy, and the up-regulation of endogenous LCAT through the administration of drugs.

In one embodiment the level of LCAT level and/or activity is increased by direct administration of LCAT. Preferably the LCAT administered in the methods according to the disclosure is recombinantly produced human LCAT (e.g., using animals, mammalian cells, fungi, insect cells or plants as a recombinant protein expression system). Methods of producing proteins recombinantly is well known in the art. LCAT may also be obtained by any suitable methods e.g., isolation from human plasma. LCAT for can be prepared in stable bulk or unit dosage forms. In one embodiment the level of LCAT activity is increased through the use of gene therapy. As used herein, "gene therapy" refers to the transfer and, preferably, stable integration of new genetic information into cells in a subject. Methods of increasing LCAT activity levels by gene therapy involves transfecting cells with a nucleic acid that comprises a nucleic acid sequence coding for expression of LCAT. The transfected cells express LCAT and secrete it into the plasma of the subject. The cells are transfected in sufficient number or for such high expression of LCAT that they increase the amount of LCAT to a therapeutically effective level. Genes encoding LCAT may be introduced into the subject by any suitable method. In one embodiment, the genes are introduced into cells of the individual in vivo by means of expression vectors. In another embodiment, the genes are introduced into cells ex-vivo, and transfected cells that express and secrete LCAT are administered to the subject. In the in vivo approaches, liver cells are useful targets for transfection. Liver cells produce LCAT, so they possess the processing machinery for making the enzyme recombinantly. Furthermore, vectors injected into the blood stream quickly pass through the liver, so liver cells are quickly exposed to the vectors. Hematopoietic stem cells also are useful targets for gene therapy because they multiply rapidly, thereby creating more cells capable of producing LCAT. Ex-vivo approaches also are attractive because they allow more control over the transfection process. For example, transfected cells can be tested and the ones which express LCAT in the highest amounts can be selected. Hematopoietic stem cells can be taken from the subject, transfected ex vivo and reintroduced into the subject. Therefore, in one embodiment, the cells are cells from the subject. Methods of transfecting genes into mammalian cells, either in vivo and ex vivo, and obtaining their expression are well known to the art.

The present disclosure relates to methods of modulating lipid content of red blood cell membranes by increasing LCAT levels and/or activity above normal human LCAT levels. One embodiment of the disclosure is a method of treating a patient having a condition characterized by red blood cells dysfunction comprising administering to the subject a therapeutically effective amount of LCAT. Another embodiment of the disclosure is a method of treating a patient having a condition characterized by red blood cells dysfunction comprising administering to the subject a therapeutically effective amount of a drug which increases the endogenous production of LCAT or increases LCAT activity. In particular embodiments the drug is a small molecule therapeutic agent.

Some embodiments are directed to methods of normalizing FC content of RBC cellular membranes by increasing LCAT levels or increasing LCAT activity in a subject in need thereof. One embodiment according to the present disclosure is a method of treating a patient having a condition which is characterized by having RBC with increased FC content by administering a therapeutically effective dose of LCAT to a patient in need thereof. Increasing LCAT levels rapidly cause the net transfer of FC from RBC to HDL, thus changing the composition of the RBC membrane to a more fluid state. This action increases the oxygenation of the RBC, improves the rheology (increase deformability, flow, decrease phosphatidylserine externalization, decrease the propensity for adhesion and aggregation) decrease anemia (decrease the mechanical stress and destruction associated with decreased deformability, increasing the life of the RBC), and increase the ability of the RBC to oxygenate tissue, especially peripheral tissues. In some embodiments erythropoiesis is increased following the administration of a therapeutically effective amount of LCAT. In some embodiments nitric oxide function is increased following the administration of a therapeutically effective amount of LCAT. There are many conditions in which the cell membranes of the RBC have increased levels of FC in relation to phospholipid levels. Increased FC content in blood cell membranes is present in a number of disease states including, but not limited to, sickle cell disease, diabetes, thalassemia, rheumatoid disease, autoimmune disease, arthritis, liver disease, cirrhosis, hepatitis, acanthocytosis, sepsis, dementia, anemia, or microvascular disorders, inflammatory disorders, parasitic disease, erectile dysfunction, cancer, pre-eclampsia, critical illness or trauma.

Although not a primary pathology in these diseases, the change in RBC composition and function leads to exacerbation of the morbidity of the underlying disorders. Thus, one embodiment of present disclosure is a method of treating a patient with sickle cell disease, diabetes, thalassemia, rheumatoid disease, autoimmune disease, arthritis, liver disease, cirrhosis, hepatitis, acanthosytosis, sepsis, dementia, anemia, or microvascular disorders, inflammatory disorders, parasitic disease, erectile dysfunction, cancer, pre-eclampsia, critical illness or trauma by administering a therapeutically effective dose of LCAT to a patient in need thereof.

Hemoglobin gene mutations such as in sickle cell disease (SCD), thalassemias and hemoglobin E (HbE) can result in a variety of pathologies which decrease RBC deformability and ability to carry/deliver oxygen. As an example, SCD is an inherited disorder, caused by a single amino acid replacement in the beta-globulin subunit of hemoglobin (HbS). Under low oxygen conditions, HbS polymerizes (aggregates), leading to changes in the shape of the RBCs from normal concave to "sickle-shaped". The formation of rigid HbS polymers decreases RBC elasticity or deformability, which is detrimental to their function, since they have to be able to repeatedly pass through capillaries four times smaller than their own size to oxygenate tissues. Therefore, sickling leads to vasoocclusive disease due to occlusion of postcapillary venules of all sizes and increased RBC fragility, leading to lysis and hemolytic anemia. Although sickling under low oxygen conditions causes acute crises and the major problems associated with the disease, the RBCs from patients that are not sickled, under normal oxygen conditions, have more rigid membranes with decreased deformability and increased aggregability. Chemical analysis of erythrocyte membranes from SCD also demonstrates increased FC content. Additionally, these patients usually have low HDL with a decreased CE content, inferring a decreased LCAT activity or functional LCAT deficiency. In fact, in one study, LCAT activity was shown to be decreased by 30% in patients with SCD. Accordingly, one embodiment of the current disclosure is a method of treating a patient having sickle cell disease by administering to a patient in need thereof, a therapeutically effective amount of LCAT.

Injecting high levels of LCAT, for example, an amount that results in a doubling of the endogenous activity to 1000-times the endogenous activity of LCAT in SCD patients, would force a movement of FC from RBC and concomitantly increasing plasma HDL-C levels. A reduction in the FC content of the RAC would lead to an increase in the ability of the RBC to deform and improve the rate of $O_2$ exchange. The improved function of the RBC may lessen the occlusive events due to both improved flow properties of blood and decreased rate of sickling (due to better re-oxygenation of the RBC). In another embodiment the administration of a therapeutically effective amount of LCAT to a patient in need thereof, increases RBC deformability and RBC oxygenation. In some embodiments the RBC life-span is increased following the administration of LCAT.

In liver disease RBC cholesterol is increased and anemia often occurs. LCAT therapy will normalize the RBC cholesterol, restore normal shape and function of the effected RBCs, decreasing RBC destruction, increasing life-span thus reducing the propensity for anemia. Therefore another embodiment is a method of treating a patient having anemia by administering to a patient, a therapeutically effective amount of LCAT.

Target cell and spur cell anemia (Acanthocytosis): Target and spur cells have an increased FC content leading to decreased function and increased hemolysis and anemia.

In conditions such as sepsis, rheumatic diseases and inflammatory disorders (including anemia of inflammation) there are myriad pathologies such as decreased RBC deformability and abnormal rheology which lead to further complications. Damage to tissues and organ systems due to decreased oxygenation and increased RBC aggregation leads to increased morbidity and mortality from the initial inflammatory insult. Thus another embodiment is a method reducing RBC aggregability by administering, to a patient in need thereof, a therapeutically effective amount of LCAT. LCAT can also act upon oxidized phospholipids generated during inflammation. The oxidized lipids are very reactive, and can increase damage to cells and organ systems. Normalizing RBC membrane lipids would improve flow and tissue oxygenation, and decrease the concentration of reactive oxidized lipids. This will be useful post-surgery, where occult infections can decrease RBC function, increasing wound-healing time.

Microvascular disorders may occur when there is an increase in RBC FC, thereby causing rigidity, increased adhesion and aggregability of the RBCs. These changes are magnified in the low flow (or low pressure) found in capillaries and venules. When RBCs are unable to deform properly, their transit is slowed to a greater extent in these small vessels. With the increased propensity for aggregation and adhesion, there is a greater chance of blockages in the peripheral vessels. In organs where the microvasculature is critical for normal function (e.g., eyes, ears, brain, kidney, penis, lungs), repeated ischemic events in these vessels could lead to loss of function (e.g., blindness, hearing loss, kidney failure, ischemic microvascular brain disease (e.g., dementia, Alzheimer's), erectile dysfunction). LCAT treatment would decrease RBC FC improving RBC rheology, decreasing risk of further blockages and end organ damage.

As demonstrated in Example 1 of the present disclosure, mice with approximately 30-fold the normal level of LCAT activity had increased RBC mass as compared to normal mice, demonstrating that LCAT activity is a major factor in regulating RBC mass, and can be rate-limiting in this regard.

Thus, administering a high dose of LCAT, for example, from 1-times to 1000-times the endogenous level of LCAT or from 1-times to 500-times the endogenous level of LCAT, or from 1-times to 100-times the endogenous level of LCAT to a patient having a condition characterized by abnormal rheology (anemia, decreased deformability, increased aggregation, decreased flow, decreased RBC life-span) would result in an improvement of the condition.

Thus, another embodiment is a method of treating a patient with sickle cell disease, diabetes, thalassemia, rheumatoid disease, autoimmune disease, arthritis, liver disease, cirrhosis, hepatitis, acanthosytosis, sepsis, dementia, anemia, or microvascular disorders, inflammatory disorders, parasitic disease, erectile dysfunction, cancer, pre-eclampsia, critical illness or trauma by administering a therapeutically effective dose of LCAT. Yet another embodiment of the present disclosure is a method of mating a patient having sickle cell disease, diabetes, thalassemia, rheumatoid disease, autoimmune disease, arthritis, liver disease, cirrhosis, hepatitis, acanthosytosis, sepsis, dementia, anemia, or microvascular disorders, inflammatory disorders, parasitic disease, erectile dysfunction, cancer, pre-eclampsia, critical illness or trauma by administration of a drug that increases LCAT activity or LCAT level. In preferred embodiments the drug is a small molecule therapeutic. In another embodiment the LCAT level and/or LCAT activity is increased using gene therapy.

Another embodiment is a method of treating a patient with an Alzheimer's related dementia by administering a therapeutically effective dose of LCAT. Another embodiment is a method of treating a patient with sickle cell disease, diabetes, thalassemia, rheumatoid disease, autoimmune disease, arthritis, liver disease, cirrhosis, hepatitis, acanthosytosis, sepsis, dementia, anemia, or microvascular disorders, inflammatory disorders, parasitic disease, erectile dysfunction, cancer, preeclampsia, critical illness or trauma by administering a therapeutically effective dose of a modified LCAT. In some embodiments the modified LCAT comprises a conservative amino acid substitution. In one embodiment the modified LCAT comprises a substitution at position F1, L3, L4, N5, L7, C31, N384 or E416. In various embodiments the modified LCAT comprises an amino acid substitution at position 31. In other embodiments the modified LCAT comprises a C31Y substitution and a substitution at one or more of amino acid residues F1, L4, L32, or N34. In another embodiment the modified LCAT comprises a C31Y substitution and one or more of the following substitutions: F1S, F1W, L4M, L4K, N34S, L32F, or L32H. In various embodiments the modified LCAT comprises one or more of the following substitutions: F1A, F1G, F1I, F1L, F1M, F1P, F1V, F1Y, F1T, F1Q, F1N, F1D, L3I, L3F, L3C, L3W, L3Y, L4A, L4I, L4M, L4F, L4V, L4W, L4Y, L4T, L4Q, L4R, N5A, N5M, N5H, N5K, N5D, N5E, L7M, L7R, L7E, C31A, C31I, C31M, C31F, C31V, C31W, C31Y, C31T, C31R, C31H, N384C, N384Q, or E416C. In other embodiments the level of LCAT in the patient is increased by using gene therapy techniques. In another embodiment LCAT expression is upregulated through drug administration.

In the methods according to the present disclosure, the LCAT is generally administered to the subject in a pharmaceutical composition comprising a pharmaceutically acceptable carrier or diluent. A pharmaceutical composition may be formulated in accordance with routine procedures as a pharmaceutical composition adapted to the chosen route of administration, i.e., orally, parenterally, by intravenous, intramuscular or subcutaneous routes.

Pharmaceutical compositions suitable for the delivery of compounds of the present disclosure and methods for their preparation will be readily apparent to those skilled in the art. Such compositions and methods for their preparation may be found, for example, in Remington's Pharmaceutical Sciences, 19th Edition (Mack Publishing Company, 1995).

The compositions may take such forms as suspensions, solutions, or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use. Typically such compositions are solutions in sterile isotonic aqueous buffer. The compositions may be a hermetically sealed container such as an ampoule, syringe, or vial with or without an added preservative.

A liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

According to the present disclosure, LCAT can be used alone or in combination therapy with other drugs used to treat the foregoing conditions. Such therapies include, but are not limited to simultaneous or sequential administration of the drugs involved. For example, LCAT formulations can be administered with drugs that are commonly used as a standard of care for a particular condition. For example LCAT can be administered in combination with erythropoiesis stimulating agents (ESA) such as erythropoietin, methoxypolyethylene-glycol-epoetin-beta, darbepoetin-α, romiplostim, and epoetin-α for treatment of anemia. Or for example LCAT can be administered in combination with hydroxyurea, hydroxycarbamide, decitabine, or butyrate for treatment of sickle cell disease.

In one embodiment the therapeutically effective amount of LCAT is administered by subcutaneous injection. In another embodiment the therapeutically effective amount of LCAT is administered by intramuscular injection. In another embodiment the therapeutically effective amount of LCAT is administered by intravenous injection or infusion. In some embodiments the therapeutically effective amount of LCAT is from 1 mg to 5000 mg, or from 1 mg to 2000 mg, or from 10 mg to 5000 mg, or from 10 mg to 1000 mg, or from 10 mg to 500 mg or from 5 mg to 100 mg.

In some embodiments the therapeutically effective amount of LCAT is from 1-times to 1000-times, from 25-times to 1000 times, from 50-times to 1000-times, from 1-times to 100 times, from 50-times to 500-times, or from 1-times to 500-times the endogenous level of LCAT.

The specific dosage used can vary. For example, the dosage can depend on a number of factors including, but not limited to, the dosing frequency, the specific activity of the recombinant LCAT enzyme, the body weight of the patient, special requirements of the patient, special conditions of the patient (e.g., abnormal kidney or liver function), the condition being treated, etc. The dosing frequency and amount may, at the physician's discretion, fall outside of the typical range given herein. These dosages are based on an average human subject having a weight of about 60 kg to 70 kg. Determination of optimum dosages for a particular patient is well-known to those skilled in the art. The physician will readily be able to determine doses for subjects whose weight falls outside this range, such as infants and the elderly.

Depending on the disorder and the patient being treated, one skilled in the art (i.e. a physician) could determine that an initial dose which is higher than following doses is appropriate. For example, a patient presenting with crisis state sickle cell disease might be administered an initial dose of 30-times the "normal" level. Once that patient's RBC oxygenation level reaches the desired level the dose would be reduced for example to 3-times the "normal" level.

The efficacy of a particular dose may be assessed by reference to biomarkers or improvement in certain physiologic parameters. Suitable biomarkers include, but are not limited to, the ratio of FC to PL, FC to membrane protein, PC to SM or HDL-C levels. Suitable physiologic parameters include, but are not limited to, reduced anemia, improved rheology as measured by an increase in RBCs, RBC deformability, blood flow, and/or RBC aggregability, osmotic fragility, or RBC oxygenation level; an increase in any one these parameters indicates improvement. Measurement of biomarker levels and parameters described above may be measured using methods that are well known in the art. For example, reduced anemia can be measured by increased hematocrit or hemoglobin or hemoglobin break-down products (e.g., unconjugated-bilirubin) measured with standard, well-established, clinical techniques. Deformability can be measured by filtration, viscometry, ektacytometry and by the use micropipettes. Aggregation may be measured by a variety of instruments including ektacytometers and aggregometers. RBC oxygenation can be measured by standard pulse oximetry and blood gas analysis; tissue oxygenation can be measured with direct probes with sialastic tonometers with oxygen sensors. One of skill in the art would understand the significance of the results and may choose to adjust the dose based on assessments such as those described above.

Figure 2:
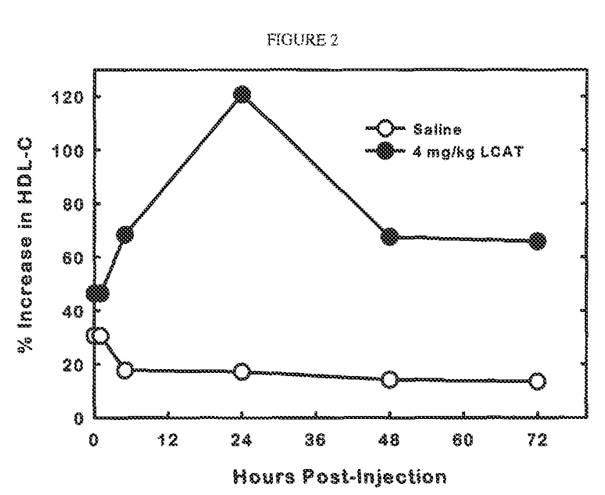
FIG. 2 is a graph depicting the increase in plasma HDL-C in human ApoA-1 transgenic mice after injection with LCAT.

As described in Example 4 and shown in FIG. 2, following administration of LCAT to human apolipoprotein A-1 transgenic mice plasma HDL-C levels increased. The increase was surprisingly rapid; plasma HDL-C levels increased by about 70% of control at 4 hours and by about 120% by 24 hours. Thus, another embodiment of the disclosure is a method of treating a patient having a condition characterized by anemia or red blood cell dysfunction comprising administering to a subject in need thereof, a therapeutically effective amount of LCAT wherein the plasma HDL-C level in the subject is rapidly increased after administration of the LCAT. In a particular embodiment the plasma HDL-C level in the subject 4 hours post administration of the LCAT is increased by at least 30% or by at least 40% or by at least 50%, or by at least 70% or by at least 80% of the plasma HDL-C level prior to LCAT administration. In yet another embodiment the plasma HDL-C level in the subject 12 hours post administration of the LCAT is increased by at least 40%, or by at least 50% or by at least 60% or by at least 70% or by at least 80%, or by at least 90% or by at least 100%, or by at least 110%, or by at least 120% of the plasma HDL-C level prior to LCAT administration. In still another embodiment the plasma HDL-C level in the subject 24 hours post administration of the LCAT is increased by at least 40%, or by at least 50% or by at least 60% or by at least 70% or by at least 80%, or by at least 90% or by at least 100%, or by at least 110%, or by at least 120%, or by at least 130%, or by at least 140%, or by at least 150% of the plasma HDL-C level prior to LCAT administration.

Figure 3:
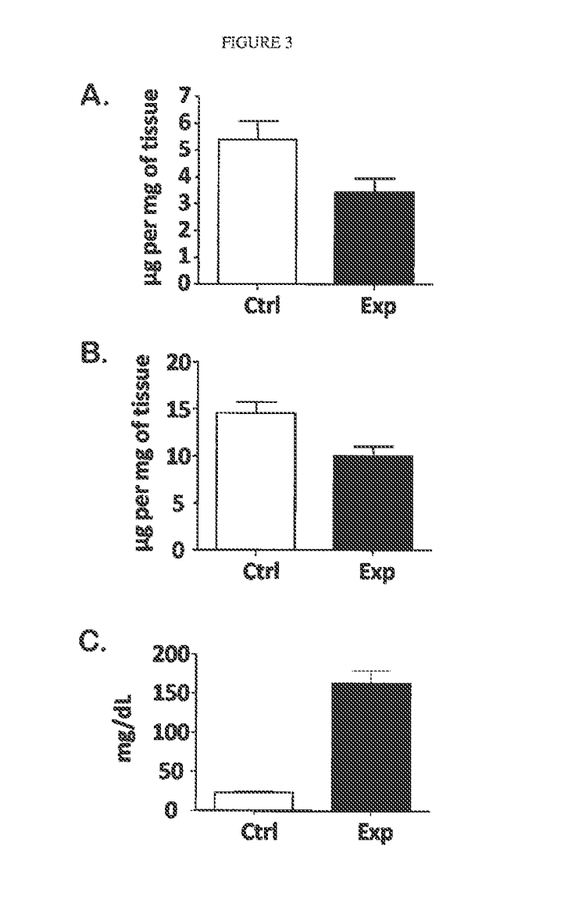
FIG. 3 depicts the cholesterol content of tissues from LCAT-knockout/apolipoprotein A-I transgenic mice after injection with recombinant human LCAT.

As described in example 5, and shown in FIG. 3, administration of LCAT to LCAT-knockout/apolipoprotein A-I transgenic mice resulted in an increase in tissue cholesterol, (aorta and liver) an increase in plasma cholesterol levels. The combined data from examples 4 and 5 demonstrate that the injection of LCAT rapidly redistributes lipids from tissues to plasma HDL. Given the effect of LCAT injection on the cholesterol content of liver and aorta it would be expected that a similar change would be rapidly be observed in red blood cells.

A transfer of FC from RBC to HDL, should change the composition of RBC membrane to a more normal state. This action will increase the oxygenation of the RBC, improve the rheology (increase deformability, flow, decrease the propensity for adhesion and aggregation) decrease anemia (decrease the mechanical stress and destruction associated with decreased deformability, increasing the life of the RBC), and increase the ability of the RBC to oxygenate tissue, especially peripheral tissues.

In some embodiments the LCAT is self-administered by the patient either by subcutaneous or intramuscular injection. Self-administration is a preferred embodiment for chronic treatment, including, but not limited to, of patients suffering with sickle cell disease, diabetes, rheumatoid disease, or hepatitis.

Example 1

Effect of LCAT Level on Hematocrit in Mice

Blood was sampled from 3 groups of mice: LCAT deficient (LCAT-KO), LCAT over-expressing transgenic (~30× normal LCAT activity), and control C57/b6 mice. RBC membranes were isolated from the blood sample, and choline containing phospholipids were measured (Wako Phospholipids B, Richmond) as a surrogate for RBC mass or hematocrit.

RBC mass was significantly lower in the LCAT deficient mice as compared to normal mice (402±22.0 µg/ml whole blood vs. 486±25.7 µml whole blood, respectively). The anemia in the LCAT deficient mice demonstrated here is similar to the extent of anemia observed in FLD patients. Surprisingly RBC mass was significantly elevated in LCAT over-expressing transgenic mice as compared to mice with normal LCAT activity (556±20.1 µg/ml whole blood vs. 486±25.7 µg/ml whole blood, respectively). These results show that there is a positive relationship between LCAT levels and hematocrit. Additionally, and most importantly, supra-normal levels of LCAT can increase hematocrit in animals not considered anemic. These studies show that increasing levels is a viable therapeutic option for patients with anemia due a variety of causes, even in patients with normal LCAT activity.

Example 2

Phospholipid Composition of RBC Ghost Membranes Prepared from Normal and SCD Subjects (Not in Crisis)

Samples of washed RBC in phosphate buffered saline were prepared from fresh blood collected from normal subjects (n=7) and SCD patients (n=6). Fifty microliter aliquots of packed RBC were suspended in 0.95 ml phosphate-buffered saline. Lipids were extracted by combining 0.4 ml aliquots of each RBC suspension with 20 µl of a 1 mg/ml solution of I-eicosanol in ethyl acetate:acetone (2:1) (internal standard) and 2 ml of ethyl acetate:acetone:methanol (6:3:1) in glass tubes. The capped tubes were shaken for 2 minutes and then centrifuged at 2000 rpm for 5 min. The upper organic phase was transferred to 12×32 mm HPLC vials. Solvent was evaporated from the vials under a stream of N2 followed by at least 1 hr of high vacuum. The dried lipids were reconstituted in 200 µl trimethylpentane:methanol:tetrahydrofuran (95:5:2). Membrane lipids were chromatographed by high-performance liquid chromatography on a silica column. Phosphatidylcholine (PC) and sphingomyelin (SM) were detected and quantitated with an evaporative light-scattering detector. The results show that the RBC lipids in SCD patients are enriched in PC and diminished in SM content, compared to normal subjects (FIG. 1), resulting in an increase in the PC/SM ratio from 0.67 to 0.98 for control and SCD, respectively. The SCD RBC analyzed in this study exhibit a phospholipid composition pattern that is distinct from normal RAC. The SCD RAC lipid composition is analogous to that reported for RAC in other cases of low plasma LCAT activity.

Example 3

Preparation of Recombinant Human Lcat

The plasmid pCMV6-XL4/LCAT encoding human LCAT protein was purchased from Origene Technologies (Rockville, Md.) and ligated into pcDNA3.1/Hygro (Invitrogen, Carlsbad, Calif.). The pcDNA3.1 vector was transfected into HEK293f cells. Stably-transfected cells were selected with 200 µg/ml hygromycin B and grown in Freestyle 293 serum-free medium (Invitrogen) in 10 L shake flasks for 4 days. The rhLCAT was isolated from the culture medium by precipitation with zinc chloride followed by batch capture and elution with phenylsepharose.

Example 4

HDL Cholesterol Increase in Human Apolipoprotein A-I Transgenic Mice Injected with LCAT Male transgenic mice expressing the human apolipoprotein A-I gene (Jackson Laboratory) were maintained on a normal chow diet, ad libitum. The mice were given a single intravenous injection of saline or recombinant human LCAT in saline (4 mg/kg) via the retro-orbital sinus. Blood was collected at the orbital plexus in isoflurane-anaesthetized animals at 0, 1, 4, 24, 48 and 72 hours post-injection. Plasma cholesterol concentration was determined with commercial enzymatic assay kits. The amount of cholesterol in HDL (HDL-C) was determined by agarose gel electrophoresis with the SPIFE system from Helena Labs. FIG. 2 shows that the mice that were administered LCAT showed a significant increase in the levels of plasma HDL-C by as much as 120% of control. The HDL-C level remained at increased levels for the duration of the experiment (72 hours). The rise in plasma HDL was surprisingly rapid showing an increase of about 70% of control at 4 hours and about 120% by 24 hours.

Example 5

Effect of LCAT Infection on Cholesterol Content in Tissues of LCAT-Knockout/Apolipoprotein A-I Transgenic Mice Transgenic mice expressing human apolipoprotein A-I (Jackson Laboratory) were cross-bred with LCAT-KO mice to obtain LCAT-KO/apoA-I-Tg mice. The LCAT-KO/apoA-I-Tg mice were maintained on normal rodent chow, ad libitum. Intravenous (IV) injections of saline or 0.4 mg LCAT were performed daily for 4 days via the retro-orbital sinus. Animals were sacrificed on the fifth day. Animals were anaesthetized and exsanguinated by perfusion with heparinized saline. A liver lobe and the aorta were removed front each animal and extracted with a chloroform and methanol solution. The cholesterol in the lipids recovered from the extracted tissues was measured with a commercial enzymatic assay kit.

FIG. 3 shows the cholesterol content of (A) liver, (B) aorta and (C) plasma for mice injected with saline (Ctrl) or LCAT (Exp). Treatment with LCAT significantly reduced the levels of cholesterol in the liver and aorta and significantly raised the plasma cholesterol level. The combined data from examples 4 and 5 demonstrate that the injection of LCAT rapidly redistributes lipids from tissues to plasma HDL. Given the effect of LCAT injection on the cholesterol content of liver and aorta it would be expected that a similar change would be observed in red blood cells.

Example 6

A child (30 kg) in sickle cell crisis is admitted to the hospital. Along with standard of care treatment, he is infused with 5 mg/kg of recombinant human LCAT (rhLCAT) over a 1-hour period in a total of 100 ml saline. Following treatment, blood oxygen levels are measured and have improved. As the crisis abates, red cell morphology and physical characteristics (RBC deformability, RBC aggregability, and osmotic fragility) are measured and the results are compared to results from blood sample taken upon admittance. Improvements in RBC physical characteristics and oxygenation are maintained with weekly subcutaneous injections of rhLCAT at a dose of 0.5 mg/kg.

Example 7

A 35 year old female (55 kg) presents with rheumatoid arthritis has anemia with a hemoglobin level of 9 g/dl (normal range 12-14 g/dl). A blood sample is taken, and demonstrates that her red blood cells are less deformable and aggregate more easily than normal red blood cells. The patient is prescribed weekly injections of rhLCAT at a dose of 1 mg/kg to be administered subcutaneously. Hematocrit and hemoglobin levels are measured after 6 weekly injections and are found to have increased 20%. After 6 months treatment, hemoglobin is 14 g/dl. The physician decides to maintain the patient on rhLCAT at a dose of 1 mg/kg injected bi-weekly.

Example 8

A 65 year old male (80 kg) is scheduled for quadruple bypass surgery. The patient is advised to stop taking clopidogrel five days prior to surgery to reduce the chance of post-operative bleeding. In order to reduce the risk of platelet activation, thrombosis, or RBC aggregation, the patient is brought into the doctor's office for an infusion of 1 mg/kg of rhLCAT five days prior to surgery. The patient is infused with 1 mg/kg of rhLCAT directly after surgery, 7 days post-surgery, and 14 days post-surgery. After recovery (21 days post-surgery), the patient is returned to chronic clopidogrel treatment.

Example 2

Gene Transfer for Hepatic Specific Over-Expression of LCAT

A patient presents with Rheumatoid arthritis accompanied by chronic anemia. The patient is administered a dose of $4 \times 10^{12}$ adenoviral particles (AdrLCAT)/kg by injection through an intra-portal catheter. LCAT levels are monitored weekly post-treatment. At four weeks post treatment the patients has an LCAT levels of 10 mg/L, or approximately two-fold greater than the concentration in a non-arthritic subject. After 8 weeks post treatment the patient is monitor monthly. If the patient's LCAT level drops below 5 mg/L the procedure is repeated.

Example 10

A child (30 kg) in sickle cell crisis is admitted to the hospital. Along with standard of care treatment, he is infused with 5 mg/kg of recombinant human LCAT (rhLCAT) over a 1-hour period in a total of 100 ml saline. Following treatment, blood oxygen levels are measured and have improved. As the crisis abates, red cell morphology and physical characteristics (RBC deformability, RBC aggregability, and osmotic fragility) are measured and the results are compared to results from blood sample taken upon admittance. The patient then has a procedure in which a medical device is placed under the skin. The medical device comprises mammalian cells engineered to secrete active LCAT. Sufficient LCAT is released by the cells to raise the endogenous LCAT activity by greater than 100% of normal LCAT levels.

It should be appreciated that the scope of this invention is to be defined by the claims and is not to be limited by the specifically described embodiments and examples herein.

What is claimed is:

1. A method of treating anemia or red blood cell dysfunction in a patient having a condition characterized by anemia or red blood cell dysfunction wherein the condition is selected from the group consisting of sickle cell disease, diabetes, thalassemia, rheumatoid disease, an autoimmune disease, arthritis, a liver disease, cirrhosis, hepatitis, acanthosytosis, sepsis, dementia, a microvascular disorder, an inflammatory disorder, parasitic disease, erectile dysfunction, cancer, preeclampsia, critical illness and trauma, comprising administering to the patient a therapeutically effective amount of lechitin cholesterol acyltransferase (LCAT).

2. The method according to claim 1, wherein the condition is characterized by reduced hematocrit, reduced hemoglobin level, red blood cells with reduced ability to deform, reduced oxygenation, increased aggregation and adhesion, reduced nitric oxide function, decreased life-span, or any combination thereof.

3. The method of claim 1, wherein the inflammatory disorder is sepsis, rheumatoid disease, anemia of inflammation, or post-surgical inflammation; the microvascular disorder is dementia, or retinopathy; the parasitic disease is malaria, sleeping sickness, filariasis, leishmaniasis; or Alzheimer's related dementia.

4. The method of claim 1, wherein the condition is sickle cell disease, a liver disease, a parasitic disease or an inflammatory disorder.

5. The method of claim 1, wherein the amount of LCAT is an amount that increases LCAT concentration to above normal LCAT levels, or increases LCAT activity to above normal LCAT activity.

6. The method according to claim 1, wherein the amount of LCAT administered is from about 10 mg to about 5000 mg.

7. The method according to claim 1, wherein the amount of LCAT administered is between 1-times and 1000-times the normal level of LCAT.

8. The method according to claim 4, wherein the condition is sickle cell disease.

9. The method according to claim 4, wherein the condition is anemia of inflammation.

10. The method according to claim 6, wherein the amount of LCAT administered is from about 10 mg to about 1000 mg.

* * * * *

SEQUENCE LISTING

```
<160> NUMBER OF SEQ ID NOS: 1

<210> SEQ ID NO 1
<211> LENGTH: 416
<212> TYPE: PRT
<213> ORGANISM: Human

<400> SEQUENCE: 1

Phe Trp Leu Leu Asn Val Leu Phe Pro Pro His Thr Thr Pro Lys Ala
1               5                   10                  15

Glu Leu Ser Asn His Thr Arg Pro Val Ile Leu Val Pro Gly Cys Leu
            20                  25                  30

Gly Asn Gln Leu Glu Ala Lys Leu Asp Lys Pro Asp Val Val Asn Trp
        35                  40                  45

Met Cys Tyr Arg Lys Thr Glu Asp Phe Phe Thr Ile Trp Leu Asp Leu
    50                  55                  60

Asn Met Phe Leu Cys Leu Gly Val Asp Cys Trp Ile Asp Asn Thr Arg
65                  70                  75                  80

Val Val Tyr Asn Arg Ser Ser Gly Leu Val Ser Asn Ala Pro Gly Val
                85                  90                  95

Gln Ile Arg Val Pro Gly Phe Gly Lys Thr Tyr Ser Val Glu Tyr Leu
            100                 105                 110

Asp Ser Ser Lys Leu Ala Gly Tyr Leu His Thr Leu Val Gln Asn Leu
        115                 120                 125

Val Asn Asn Gly Tyr Val Arg Asp Glu Thr Val Arg Ala Ala Pro Tyr
    130                 135                 140

Asp Trp Arg Leu Glu Pro Gly Gln Gln Glu Glu Tyr Tyr Arg Lys Leu
145                 150                 155                 160
```

-continued

```
Ala Gly Leu Val Glu Glu Met His Ala Ala Tyr Gly Lys Pro Val Phe
            165                 170                 175
Leu Ile Gly His Ser Leu Gly Cys Leu His Leu Leu Tyr Phe Leu Leu
            180                 185                 190
Arg Gln Pro Gln Ala Trp Lys Asp Arg Phe Ile Asp Gly Phe Ile Ser
            195                 200                 205
Leu Gly Ala Pro Trp Gly Gly Ser Ile Lys Pro Met Leu Val Leu Ala
            210                 215                 220
Ser Gly Asp Asn Gln Gly Ile Pro Ile Met Ser Ser Ile Lys Leu Lys
225                 230                 235                 240
Glu Glu Gln Arg Ile Thr Thr Thr Ser Pro Trp Met Phe Pro Ser Arg
            245                 250                 255
Met Ala Trp Pro Glu Asp His Val Phe Ile Ser Thr Pro Ser Phe Asn
            260                 265                 270
Tyr Thr Gly Arg Asp Phe Gln Arg Phe Phe Ala Asp Leu His Phe Glu
            275                 280                 285
Glu Gly Trp Tyr Met Trp Leu Gln Ser Arg Asp Leu Leu Ala Gly Leu
            290                 295                 300
Pro Ala Pro Gly Val Glu Val Tyr Cys Leu Tyr Gly Val Gly Leu Pro
305                 310                 315                 320
Thr Pro Arg Thr Tyr Ile Tyr Asp His Gly Phe Pro Tyr Thr Asp Pro
            325                 330                 335
Val Gly Val Leu Tyr Glu Asp Gly Asp Asp Thr Val Ala Thr Arg Ser
            340                 345                 350
Thr Glu Leu Cys Gly Leu Trp Gln Gly Arg Gln Pro Gln Pro Val His
            355                 360                 365
Leu Leu Pro Leu His Gly Ile Gln His Leu Asn Met Val Phe Ser Asn
370                 375                 380
Leu Thr Leu Glu His Ile Asn Ala Ile Leu Leu Gly Ala Tyr Arg Gln
385                 390                 395                 400
Gly Pro Pro Ala Ser Pro Thr Ala Ser Pro Glu Pro Pro Pro Pro Glu
            405                 410                 415
```